United States Patent
Mangiardi et al.

(10) Patent No.: US 10,137,022 B2
(45) Date of Patent: *Nov. 27, 2018

(54) IMPLANTATION DEVICE WITH HANDLE AND METHOD OF USE THEREOF

(71) Applicant: QUALIMED INNOVATIVE MEDIZINPRODUKTE GMBH, Luhe (DE)

(72) Inventors: Eric K. Mangiardi, Charlotte, NC (US); Thomas Nissl, Winsen Luhe (DE)

(73) Assignee: QUALIMED INNOVATIVE MEDIZINPRODUKTE GMBH, Winsen (Luhe) (DE)

( * ) Notice: Subject to any disclaimer, the term of this patent is extended or adjusted under 35 U.S.C. 154(b) by 126 days.

This patent is subject to a terminal disclaimer.

(21) Appl. No.: 15/226,670

(22) Filed: Aug. 2, 2016

(65) Prior Publication Data

US 2016/0338866 A1 Nov. 24, 2016

Related U.S. Application Data

(63) Continuation of application No. 12/545,982, filed on Aug. 24, 2009, now Pat. No. 9,439,652.

(51) Int. Cl.
*A61F 2/966* (2013.01)
*A61B 17/12* (2006.01)
(Continued)

(52) U.S. Cl.
CPC ........ *A61F 2/966* (2013.01); *A61B 17/12022* (2013.01); *A61F 2/95* (2013.01);
(Continued)

(58) Field of Classification Search
CPC ....... A61F 2/966; A61F 2/95; A61B 17/12022
See application file for complete search history.

(56) References Cited

U.S. PATENT DOCUMENTS

| | | | |
|---|---|---|---|
| 5,201,757 | A | 4/1993 | Heyn et al. |
| 5,370,134 | A | 12/1994 | Chin et al. |

(Continued)

FOREIGN PATENT DOCUMENTS

| | | |
|---|---|---|
| CN | 2652421 | 11/2004 |
| CN | 102596111 | 7/2012 |

(Continued)

OTHER PUBLICATIONS

Extended European Search Report issued by the European Patent Office in European Patent Application No. 10814102.9, dated Apr. 25, 2016.

(Continued)

*Primary Examiner* — Richard Louis
(74) *Attorney, Agent, or Firm* — Ping Wang; Morris, Menning & Martin, LLP

(57) ABSTRACT

An instrument for deploying an implantable medical device into a body lumen is disclosed. The instrument comprises a base member having a base handle and a deployment extension, a first tubular member having a first tubular body and a first handle, and a second tubular member having a second tubular body and a second handle. The first tubular member fits over the deployment extension and is longitudinally slidable over the deployment extension, and the second tubular member fits over the first tubular member and is longitudinally slidable over the first tubular member. The distal ends of the deployment extension, the first tubular body, and the second tubular body are adapted to hold and deploy the implantable medical device.

20 Claims, 17 Drawing Sheets

(51) Int. Cl.
*A61F 2/95* (2013.01)
*A61B 17/28* (2006.01)
*A61B 90/00* (2016.01)
*A61F 2/06* (2013.01)
*A61F 2/04* (2013.01)

(52) U.S. Cl.
CPC ... *A61B 17/2841* (2013.01); *A61B 2017/1205* (2013.01); *A61B 2090/061* (2016.02); *A61B 2090/0811* (2016.02); *A61F 2/06* (2013.01); *A61F 2002/041* (2013.01); *A61F 2002/9517* (2013.01)

(56) References Cited

U.S. PATENT DOCUMENTS

| | | | |
|---|---|---|---|
| 5,571,168 | A | 11/1996 | Toro |
| 5,591,172 | A | 1/1997 | Bachmann et al. |
| 5,891,112 | A | 4/1999 | Samson |
| 5,968,052 | A | 10/1999 | Sullivan, III et al. |
| 6,077,258 | A | 6/2000 | Lange et al. |
| 6,143,021 | A | 11/2000 | Staehle |
| 6,383,211 | B1 | 5/2002 | Staehle |
| 6,413,269 | B1 | 7/2002 | Bui et al. |
| 6,530,933 | B1 | 3/2003 | Yeung et al. |
| 6,631,715 | B2 | 10/2003 | Kirn |
| 7,527,644 | B2 | 5/2009 | Mangiardi et al. |
| 7,547,321 | B2 | 6/2009 | Silvestri et al. |
| 9,439,652 | B2 * | 9/2016 | Mangiardi ....... A61B 17/12022 |
| 2002/0052641 | A1 | 5/2002 | Monroe et al. |
| 2002/0111666 | A1 | 8/2002 | Hart et al. |
| 2003/0060813 | A1 | 3/2003 | Loeb et al. |
| 2004/0153137 | A1 | 8/2004 | Gaschino et al. |
| 2005/0038495 | A1 | 2/2005 | Greenan |
| 2007/0073247 | A1 | 3/2007 | Ewaschuk |
| 2007/0179586 | A1 | 8/2007 | Aguirre et al. |
| 2007/0233222 | A1 | 10/2007 | Roeder et al. |
| 2007/0250150 | A1 | 10/2007 | Pal et al. |
| 2007/0270932 | A1 | 11/2007 | Headley et al. |
| 2008/0119891 | A1 | 5/2008 | Miles et al. |
| 2009/0118740 | A1 | 5/2009 | Mangiardi et al. |
| 2009/0192518 | A1 | 7/2009 | Golden et al. |
| 2009/0192600 | A1 | 7/2009 | Ryan |
| 2011/0046710 | A1 | 2/2011 | Mangiardi et al. |

FOREIGN PATENT DOCUMENTS

| | | |
|---|---|---|
| EP | 1 096 904 | 5/2001 |
| EP | 1 803 422 | 7/2007 |
| WO | 00/078246 | 12/2000 |
| WO | 07/19253 | 3/2001 |
| WO | 02/083037 | 10/2002 |
| WO | 2006072934 | 7/2006 |
| WO | 2007/098232 | 8/2007 |
| WO | 2011/028302 | 3/2011 |

OTHER PUBLICATIONS

International Search Report and Written Opinion of the International Searching Authority issued in International Patent Application No. PCT/US2012/040453 dated Dec. 14, 2012.
International Search Report (Application No. PCT/US201 0/029218, filed Mar. 30, 2010).
Written Opinion of the International Searching Authority (Application No. PCT/US2010/029218, filed Mar. 30, 2010).
U.S. Appl. No. 12/545,982, filed Aug. 24, 2009.

* cited by examiner

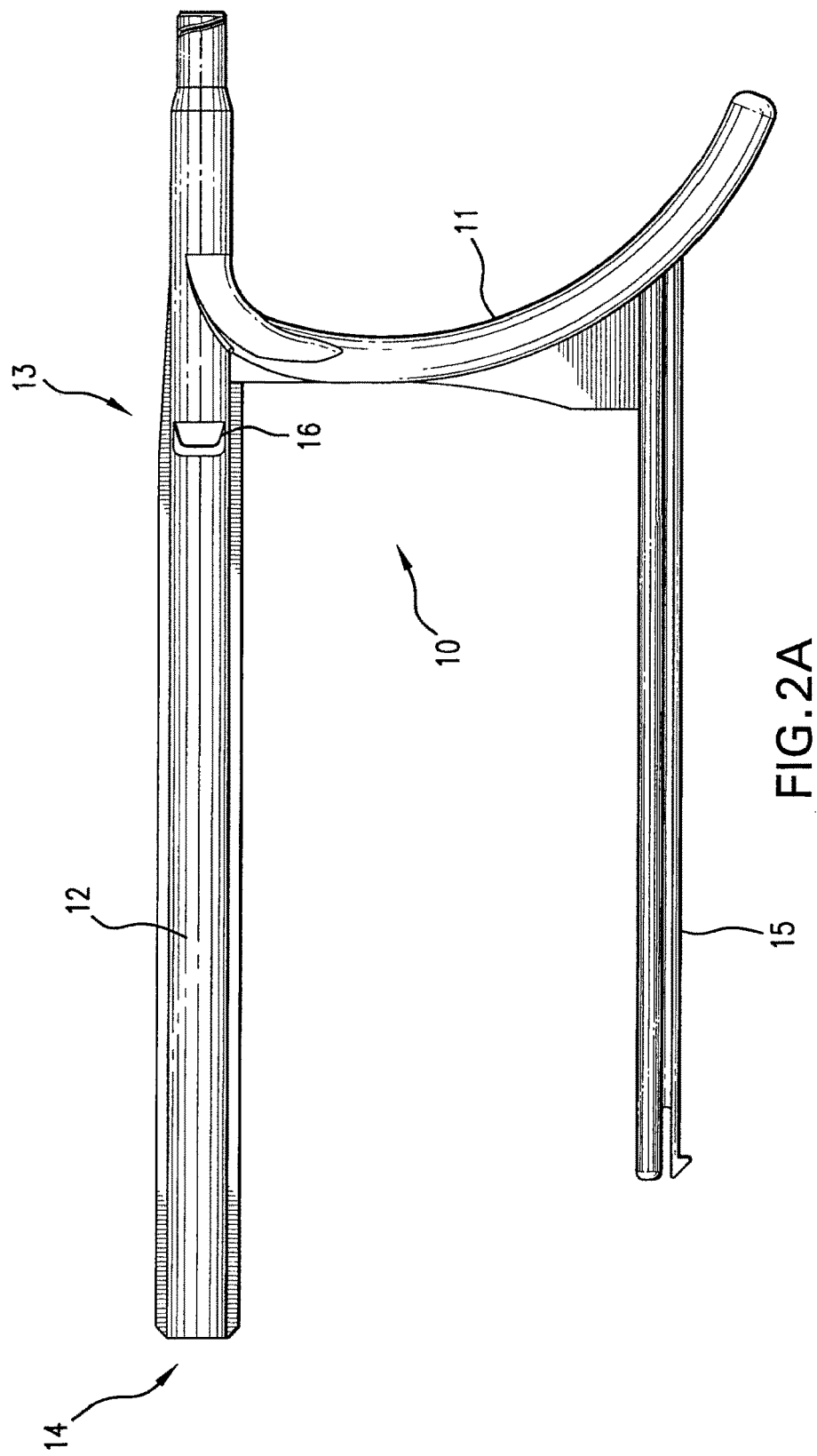

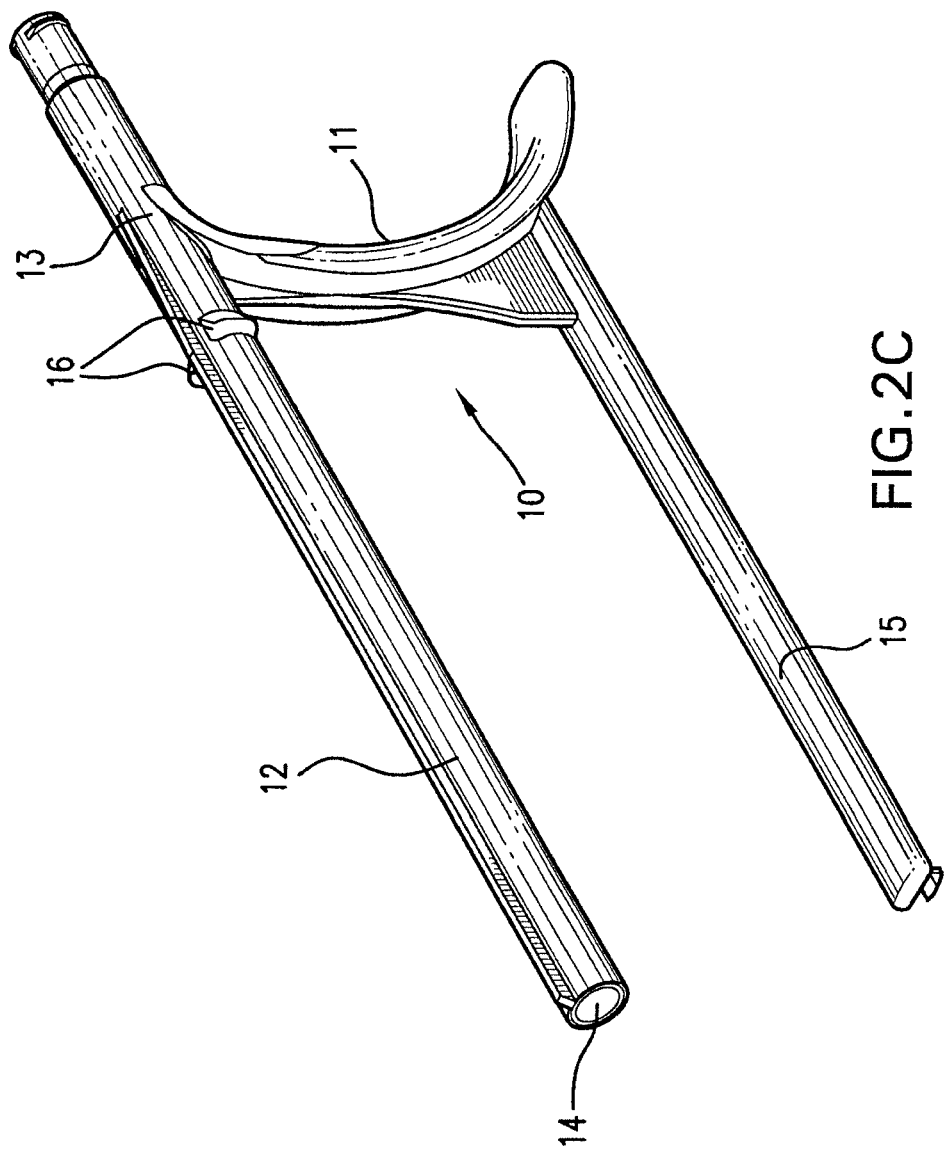

IMPLANTATION DEVICE WITH HANDLE AND METHOD OF USE THEREOF

This application is a Continuation of U.S. application Ser. No. 12/545,982, filed Aug. 24, 2009. The entirety of the aforementioned applications is incorporated herein by reference.

FIELD

The present invention relates generally to medical devices and, in particular, to a delivery system for introducing implantable medical devices into a body cavity.

BACKGROUND

Implants may be placed in the human body for a variety of reasons. For example, stents are placed in a number of different body lumens such as blood vessels and biliary ducts; vena cava filters are implanted in the vena cava to catch thrombus sloughed off from other sites within the body; and vaso-occlusive devices are used for the treatment of intravascular aneurysms.

Interventional practitioners, regardless of subspecialty have always had to demonstrate profound dexterity in order to effectively and accurately perform invasive procedures. This is particularly the case with the delivery and deployment of implantable devices where there is very little room for error with respect to placement. In order to assist with placement accuracy, many interventionalists utilize scopes, such as bronchoscopes or endoscopes, ultrasound, ct scanning, or other imaging modalities. However, handling the imaging modality and the delivery catheter can often be a clumsy process when the two devices easily disassociate from each other. Moreover, since many delivery catheters, for one reason or another, cannot be adequately managed with one hand, additional personnel are required when handling the scope and the delivery catheter.

Therefore, there is an existing need for a delivery system that allows a physician to deploy an implantable device with one hand.

SUMMARY

One aspect of the present invention relates to an instrument for deploying an implantable medical device in a body lumen. The instrument comprises a base member, a first tubular member and a second tubular member. The base member contains a base handle and a deployment extension having a distal end and a proximate end, the proximate end is connected to the base handle. The first tubular member includes a first tubular body with a distal end and a proximal end; and a first handle for controlling movement of the first tubular member. The first tubular body fits over the deployment extension and is longitudinally slidable over the deployment extension. The second tubular member includes a second tubular body with a distal end and a proximal end and a second handle for controlling movement of the second tubular member. The second tubular body fits over the first tubular body and is longitudinally slidable over the first tubular body. As such, the first handle is located between the base handle and the second handle. Further, the distal ends of the deployment extension, the first tubular body, and the second tubular body are adapted to deploy an implantable medical device via a catheter. More tubular members can be added as needed based on the length of the deployed instrument via a catheter.

In one embodiment, the base member further includes a guiding extension, the guiding extension is connected to the base handle and extends in a direction parallel to the deployment extension.

In another embodiment, the base member further comprises a coupling device for a viewing device, guide wire, or stabilization or attachment mechanism In a related embodiment, the viewing device is an endoscope, broncoscope. CT, in vivo imaging system (IVIS), or other imaging modality.

In another embodiment, the deployment extension comprises means at the distal end for attachment of the catheter.

In another embodiment, the first handle of the first tubular member comprises a stabilizing ring that fits over the guiding extension of the base member and is longitudinally slidable over the guiding extension.

In another embodiment, the first tubular member comprises interlocking means for attachment to the second tubular member.

In a related embodiment, the interlocking means includes a locking tab on the first tubular body and a matching locking hole on the second tubular body.

In another embodiment, the base handle, the first handle and the second handle are beveled handles.

In another embodiment, the first tubular member has contoured sides to facilitate single-finger control of the first tubular member.

In another embodiment, the deployment extension of the base member further comprises a compression stopper to prevent the instrument from being over deployed.

In another embodiment, the implantable medical device is a stent.

Another aspect of the present invention relates to a method for delivering an implantable medical device to a body lumen using the instrument described above. The method comprises the steps of attaching the first tubular member to the base member by sliding the first tubular body over the implantable medical device and the deployment extension, attaching the second tubular member to the base member by sliding the second tubular body over the implantable medical device and the first tubular body, attaching a proximate end of a catheter to the distal end of the second tubular body, wherein an implantable medical device is attached to a distal end of the catheter, advancing the device into the body lumen, and retracting the first tubular member and the second tubular member towards the base member to deploy the implantable medical device in the body lumen.

In one embodiment, the retracting step includes: (1) retracting the second tubular member towards the proximate end of the first tubular member; and (2) retracting the first tubular member towards the proximate end of the base member.

In another embodiment, the retracting step includes: (1) retracting the first tubular member towards the proximate end of the base member, and (2) retracting the second tubular member towards the proximate end of the first tubular member.

Further objectives, features and advantages of the invention will be apparent from the following detailed description taken in conjunction with the accompanying drawings.

BRIEF DESCRIPTION OF THE DRAWINGS

For the purposes of this disclosure, unless otherwise indicated, identical reference numerals used in different figures refer to the same component.

FIGS. 2A, 2B and 2C are perspective views of an embodiment of the base member of the delivery system 100.

DETAILED DESCRIPTION

While this invention may be embodied in many different forms, there are described in detail herein specific preferred embodiments of the invention. This description is an exemplification of the principles of the invention and is not intended to limit the invention to the particular embodiments illustrated.

Figure 1:
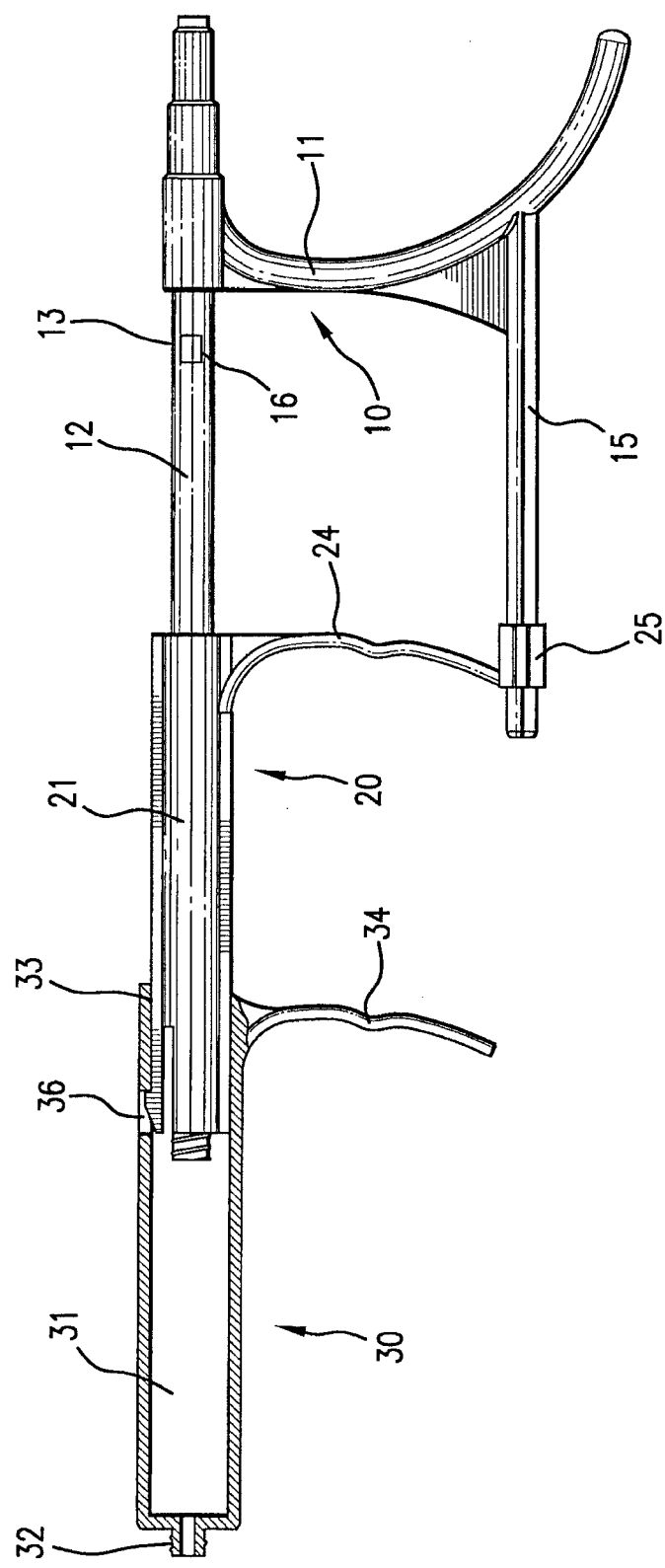
FIG. 1 shows a perspective view of an exemplary delivery system 100 in a pre-deployment configuration.
Figure 2B:
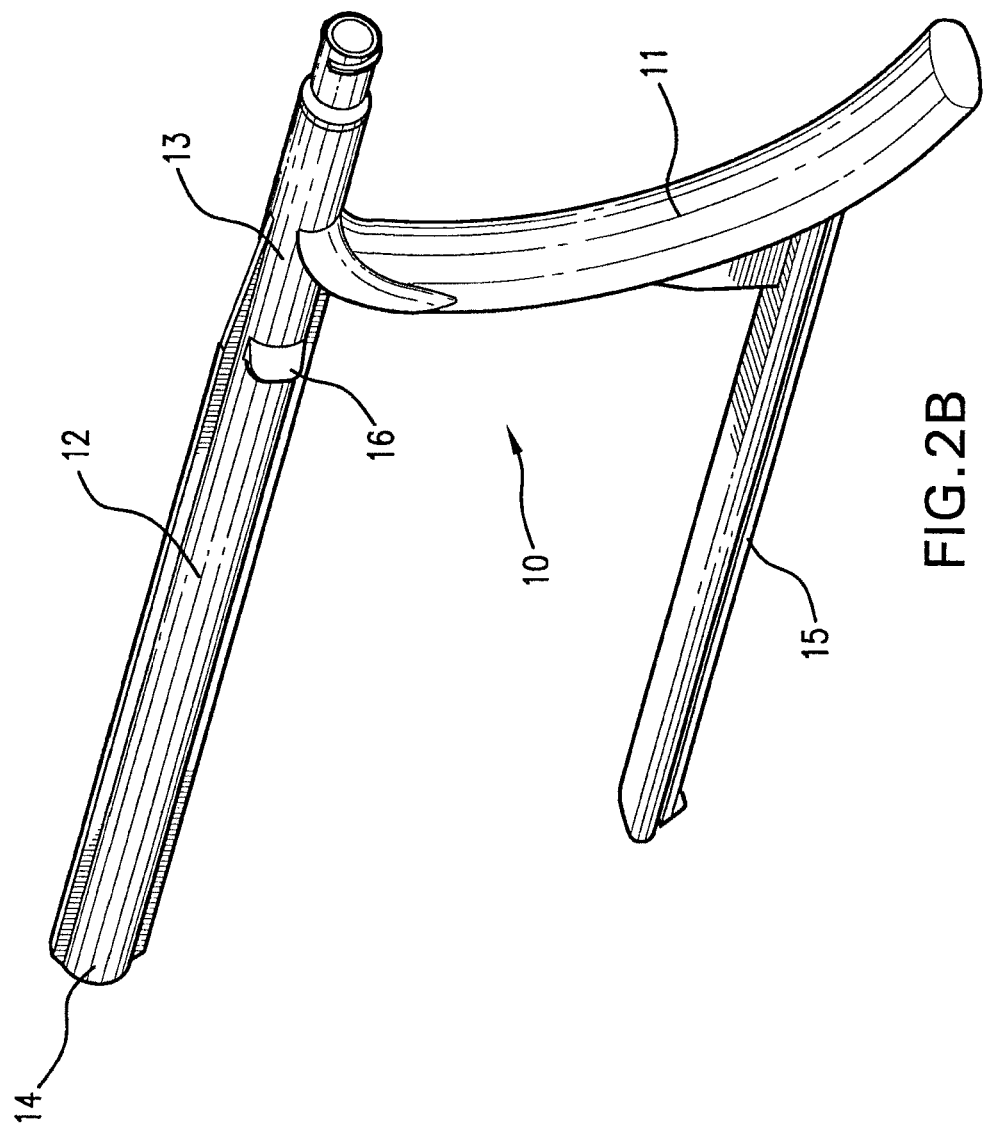

One aspect of the present invention provides a device for deploying an implantable medical device in an anatomical lumen of a patient. The device allows the user to install the implantable device with one hand. As shown in FIG. 1, an embodiment of the device 100 contains a base member 10, a first tubular member 20 that fits over the deployment extension 12 and is longitudinally slidable along the deployment extension 12, and a second tubular member 30 that fits over the first tubular member 20 and is longitudinally slidable along the first tubular member 20. As shown in FIGS. 2A-2C, the base member 10 contains a base handle 11 and a deployment extension 12. The deployment extension 12 is a rod-like structure having a proximate end 13, a distal end 14, and a pair of compression stopper 16 (one on each side of the extension 12, see e.g., FIG. 2C) near the proximate end 13 to prevent the device from being over deployed. The proximate end 13 of the deployment extension 12 is removably or permanently connected to the base handle 11. In this embodiment, the base handle 11 further contains a guiding extension 15 that matches with a stabilizing ring on the first tubular member 20 to prevent rotation of the first tubular member 20.

In another embodiment, the base member 10 further contains a scope coupling device so that an optical device, such as an endoscope or a broncoscope, may be attached to the deployment extension 12 to facilitate the deployment of the implantable medical device. In certain embodiments, the scope coupling mechanism allows for the manipulation of the scope (e.g., rotate) with respect to the base member 10 when the scope is coupled to the based member 10. In other embodiments, the base member 10 further contains a guide wire coupling device so that a guide wire may be attached to the deployment extension 12 to facilitate the deployment of the implantable medical device.

Figure 3A:
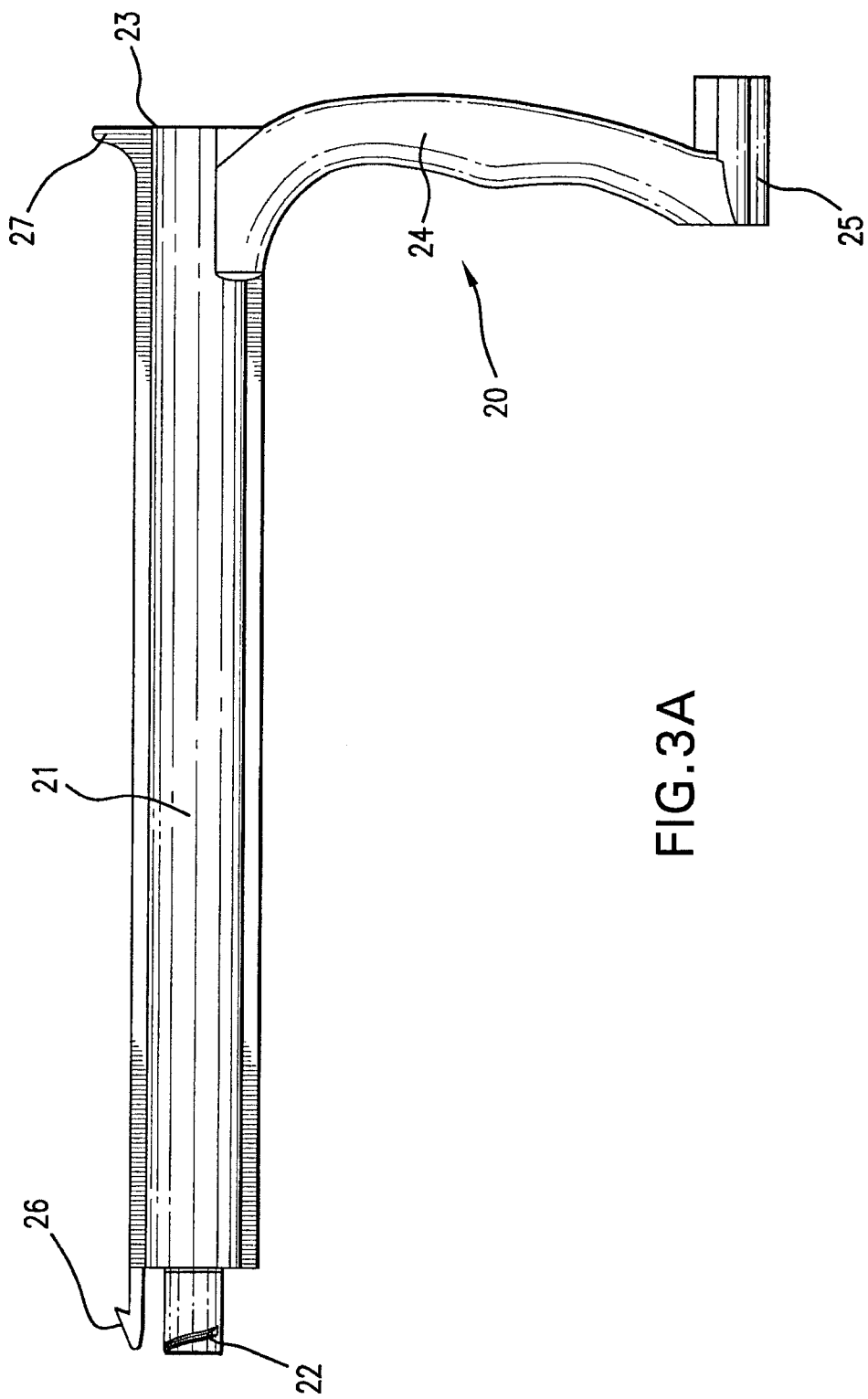
FIGS. 3A, 3B and 3C are perspective views of the first tubular member of the delivery system 100.
Figure 3B:
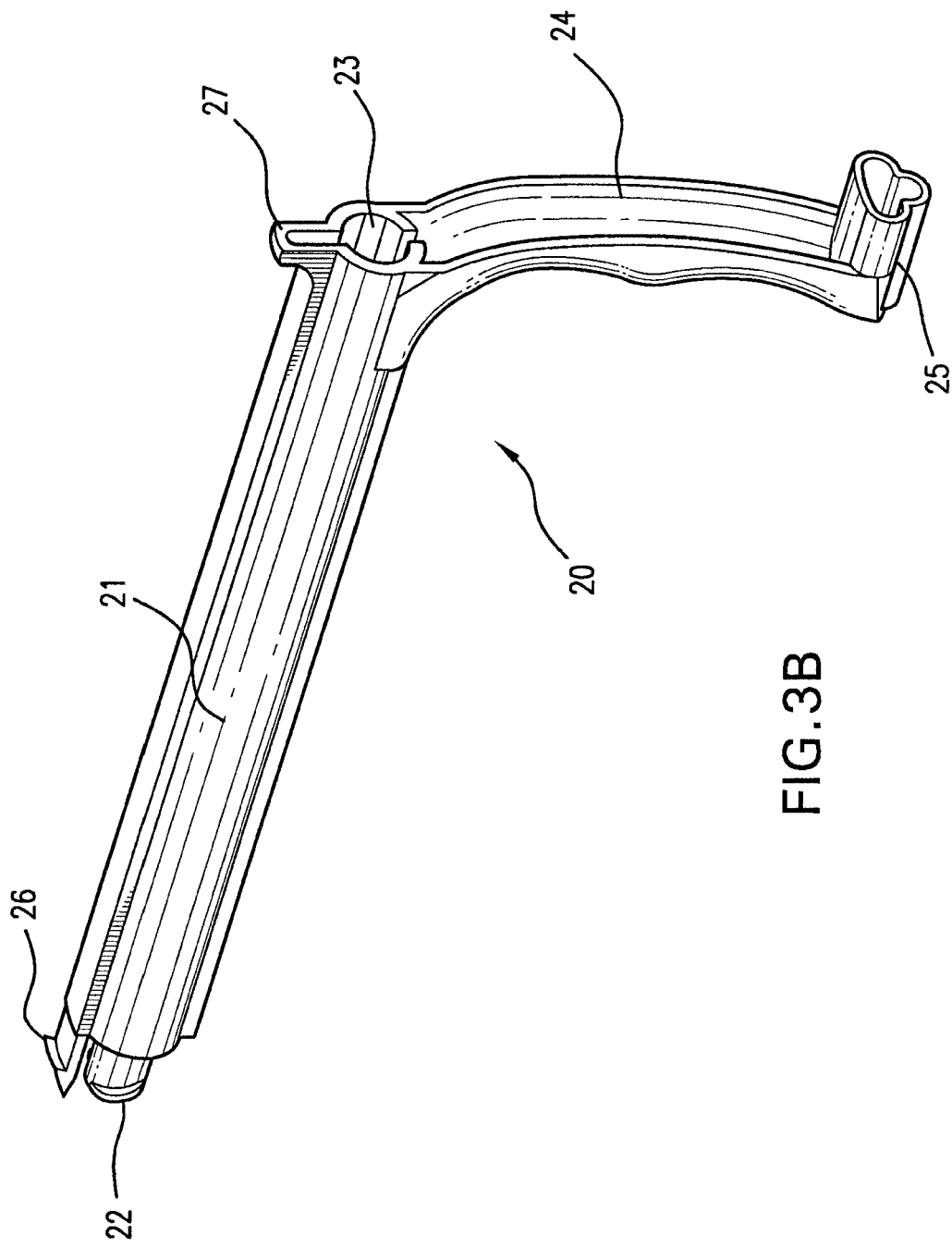
Figure 3C:
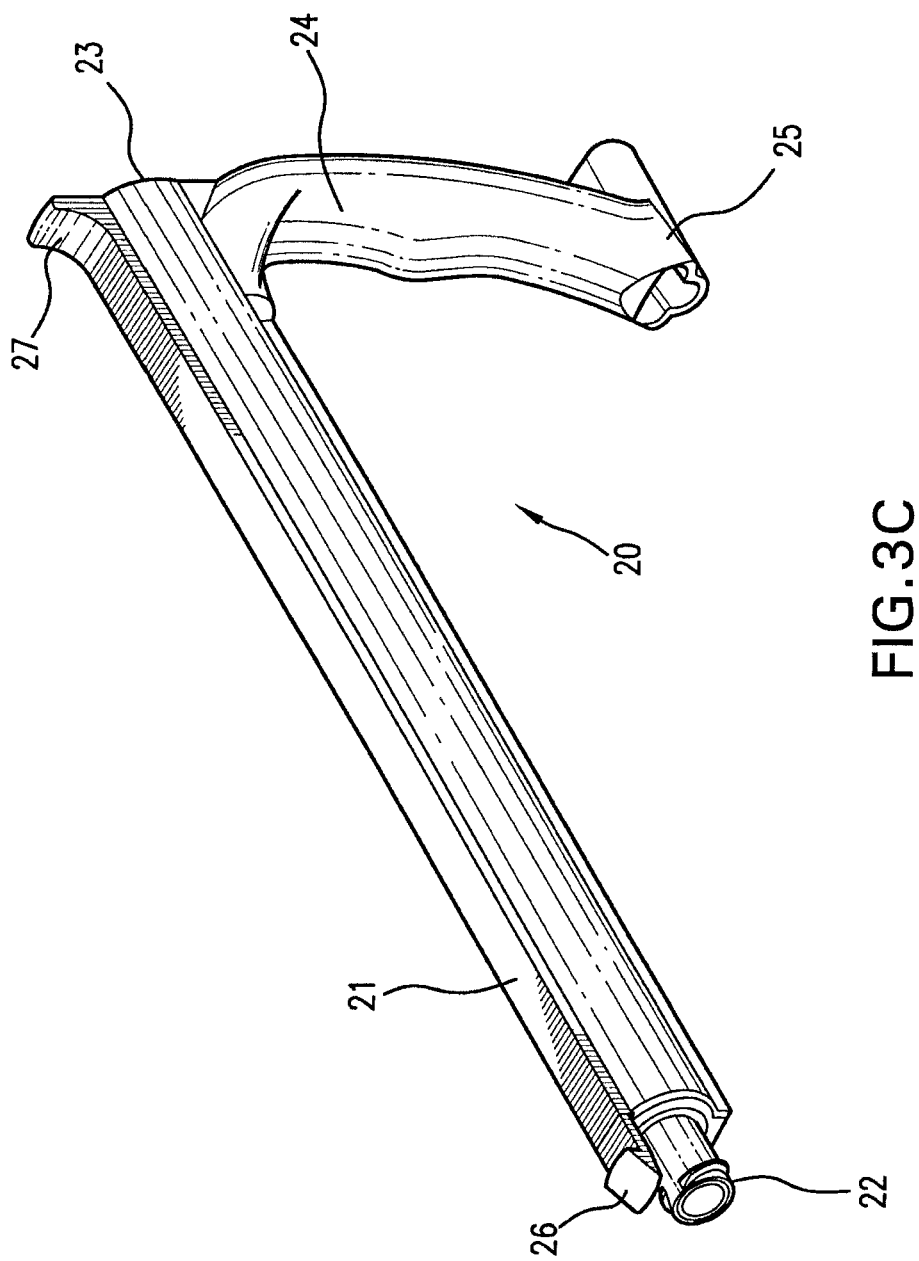
Figure 4A:
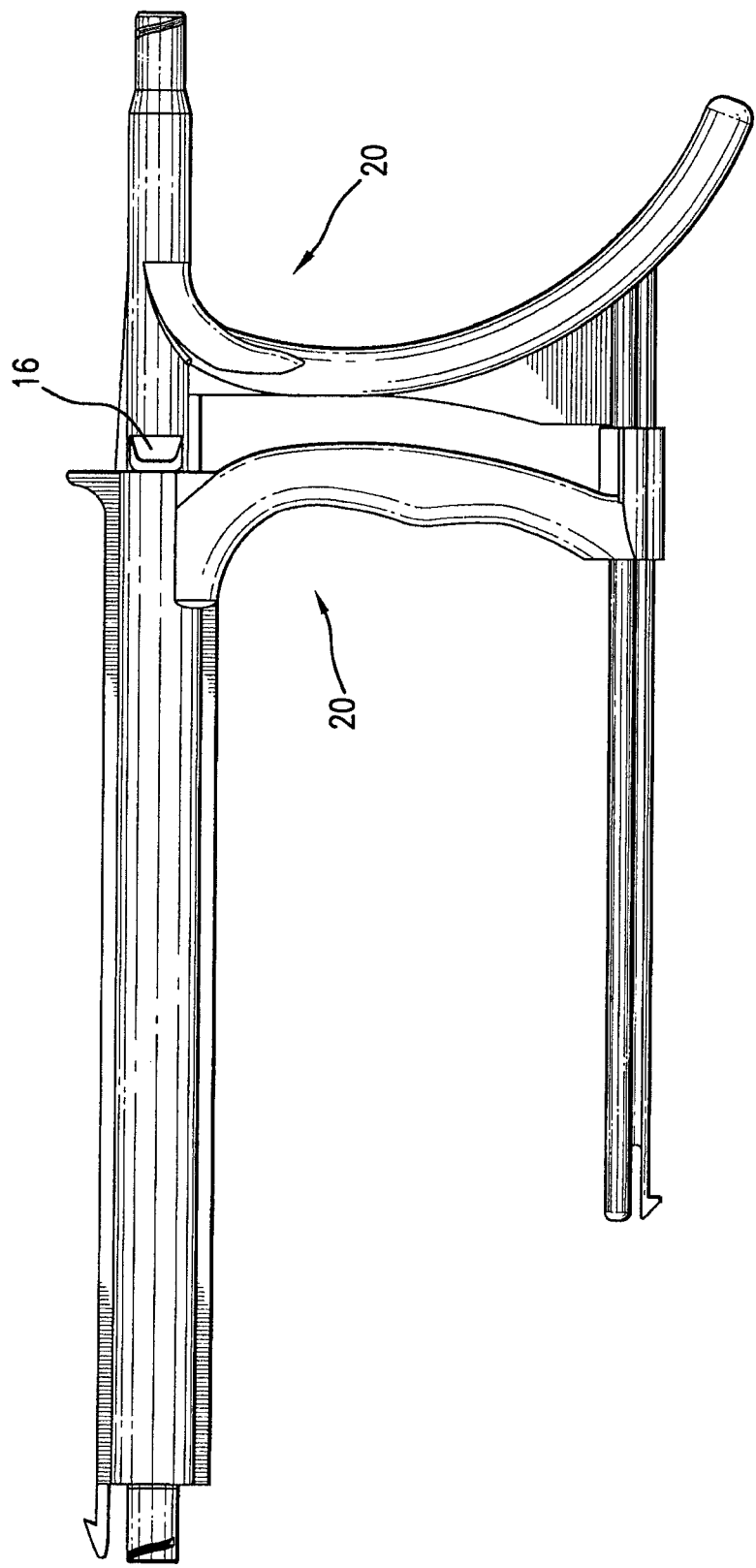
FIGS. 4A, 4B and 4C are perspective view of the first tubular member in a retracted position.
Figure 4B:
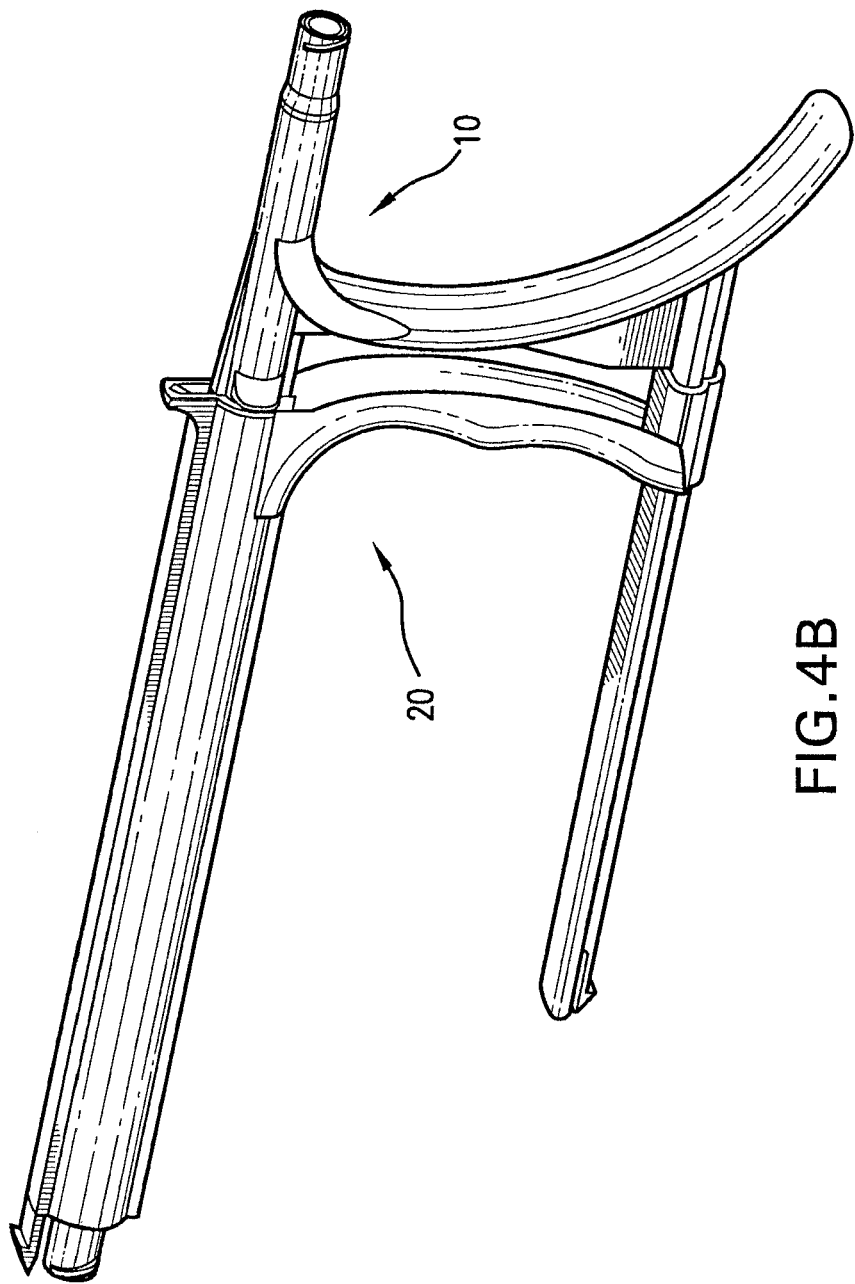
Figure 4C:
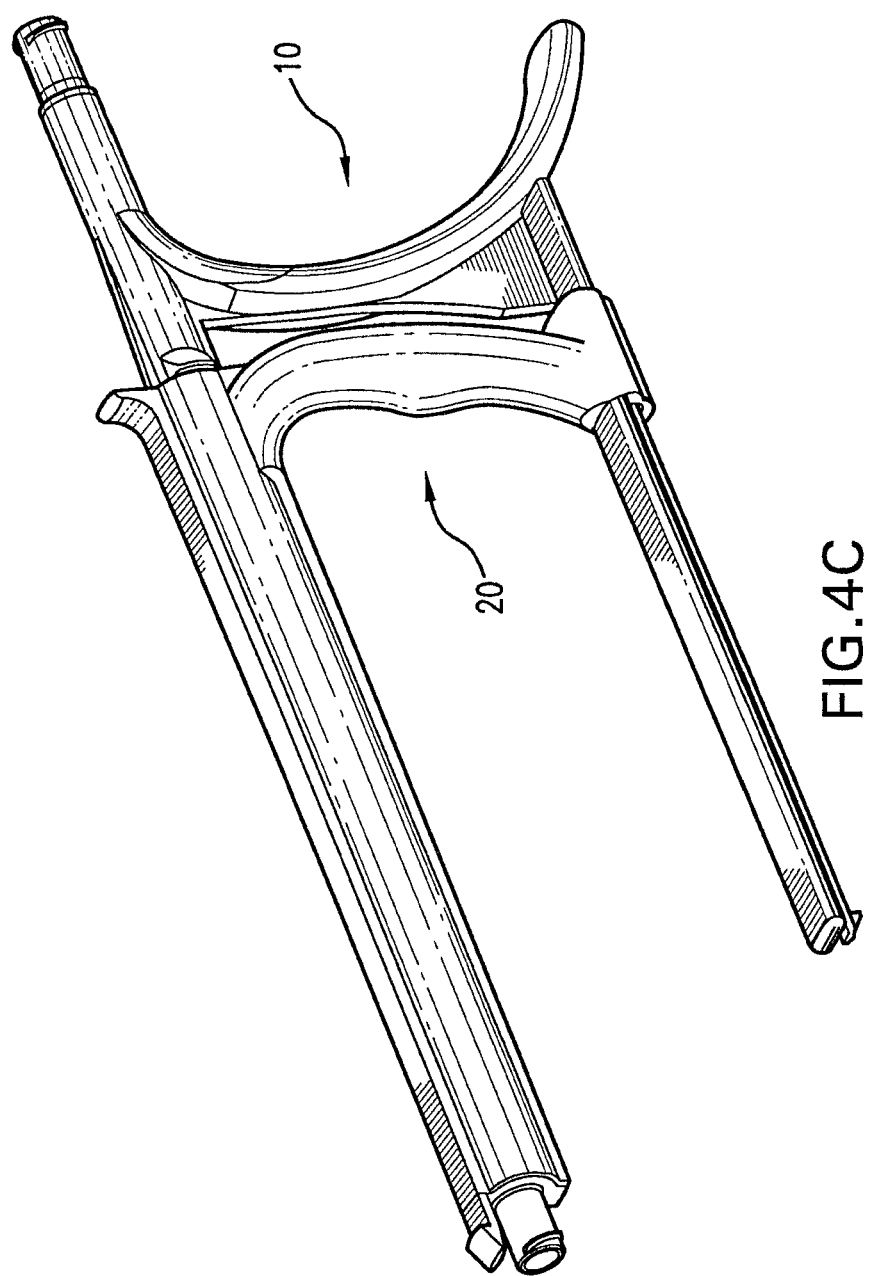

As shown in FIGS. 3A-3C, the first tubular member 20 contains a first tubular body 21 with a distal end 22 and a proximal end 23, and a first handle 24 for controlling movement of the first tubular member 20. The first tubular body 21 has a center lumen with a cross-sectional shape adopted to fit the outside contour of the deployment extension 12 and to slide longitudinally along the deployment extension 12. The first handle 24 further contains a stabilizing ring 25 that fits over the guiding extension 15 of the base handle 12. As shown in FIG. 1, the stabilizing ring 25 slides along the guiding extension 15 of the base handle 11 and prevents rotation of the first tubular member 20 along the central axis of the deployment extension 12. The first tubular member 20 is dissociable from the base member 10 by sliding off from the distal end 14 of the deployment extension 12. FIG. 4 shows the first tubular member 20 in a retracted position with the base member 10.

Figure 5A:
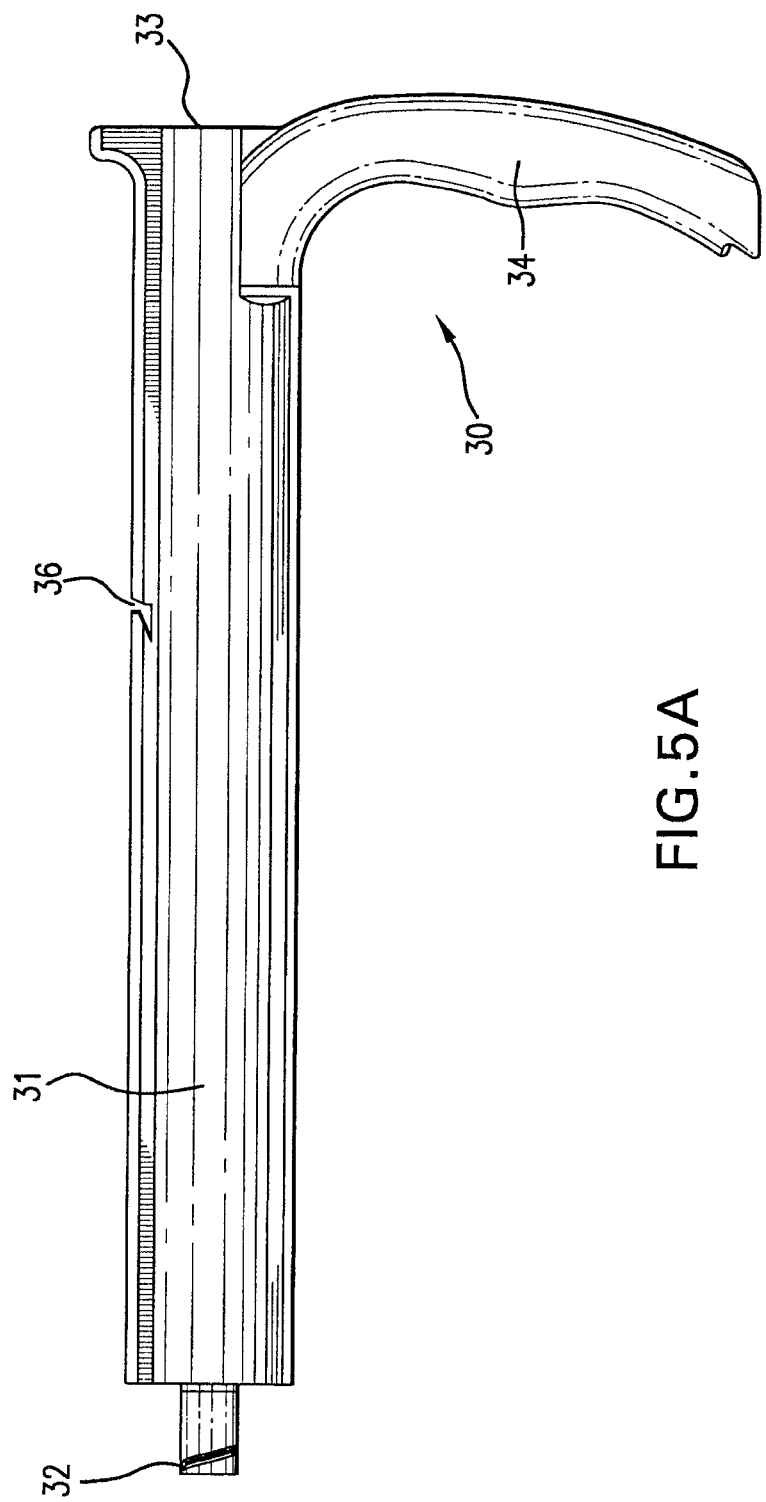
FIGS. 5A, 5B and 5C are perspective views of the second tubular member of the delivery system 100.
Figure 5B:
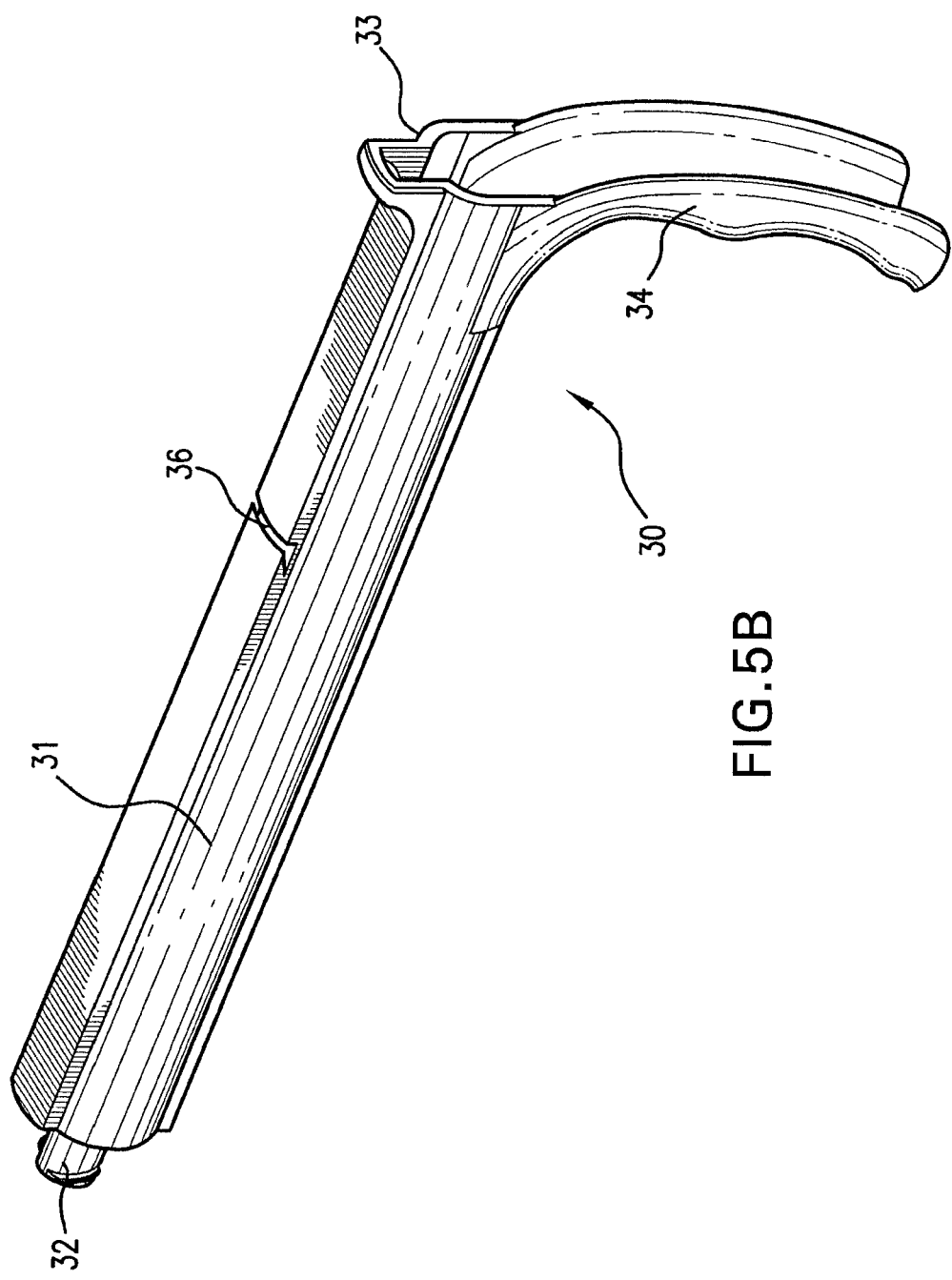
Figure 5C:
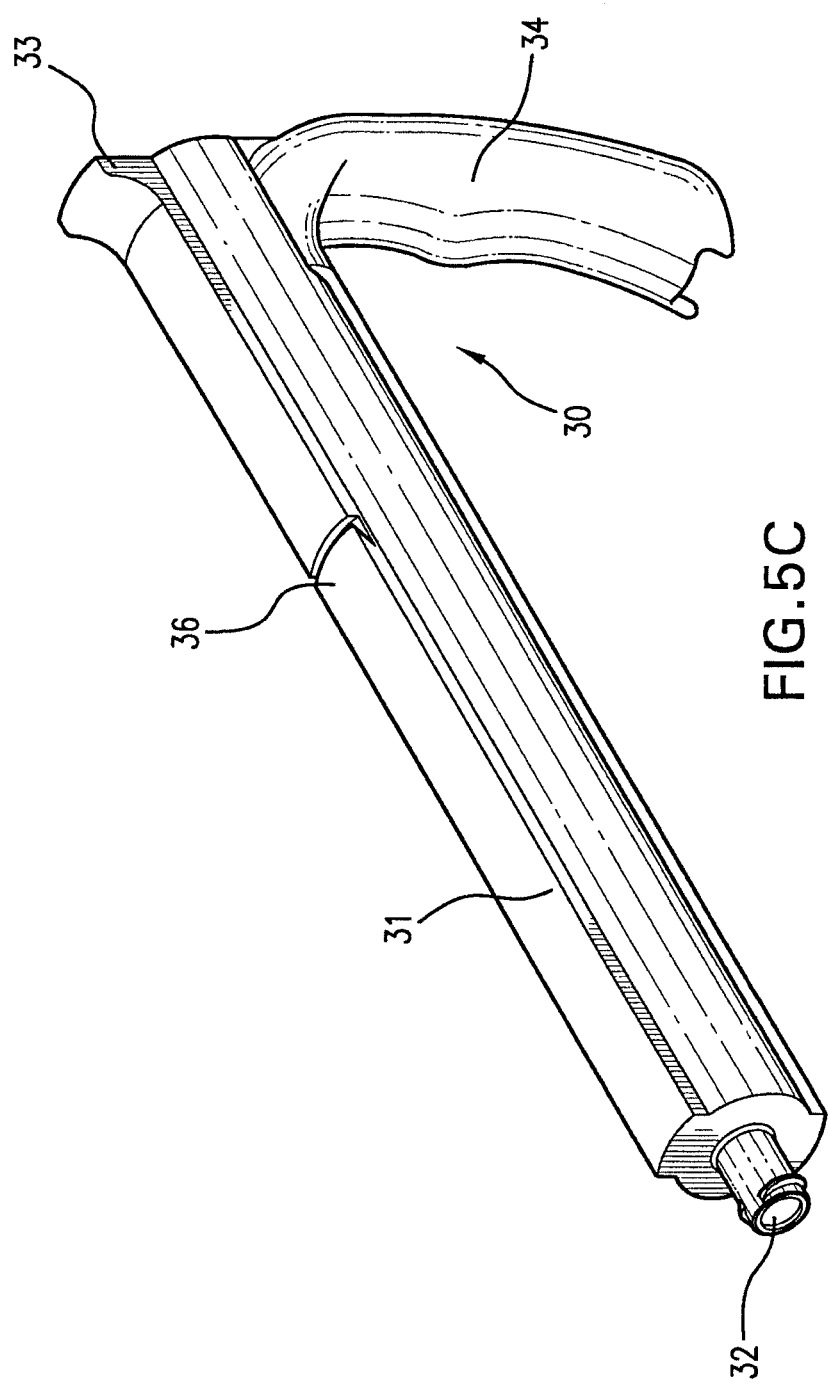
Figure 6A:
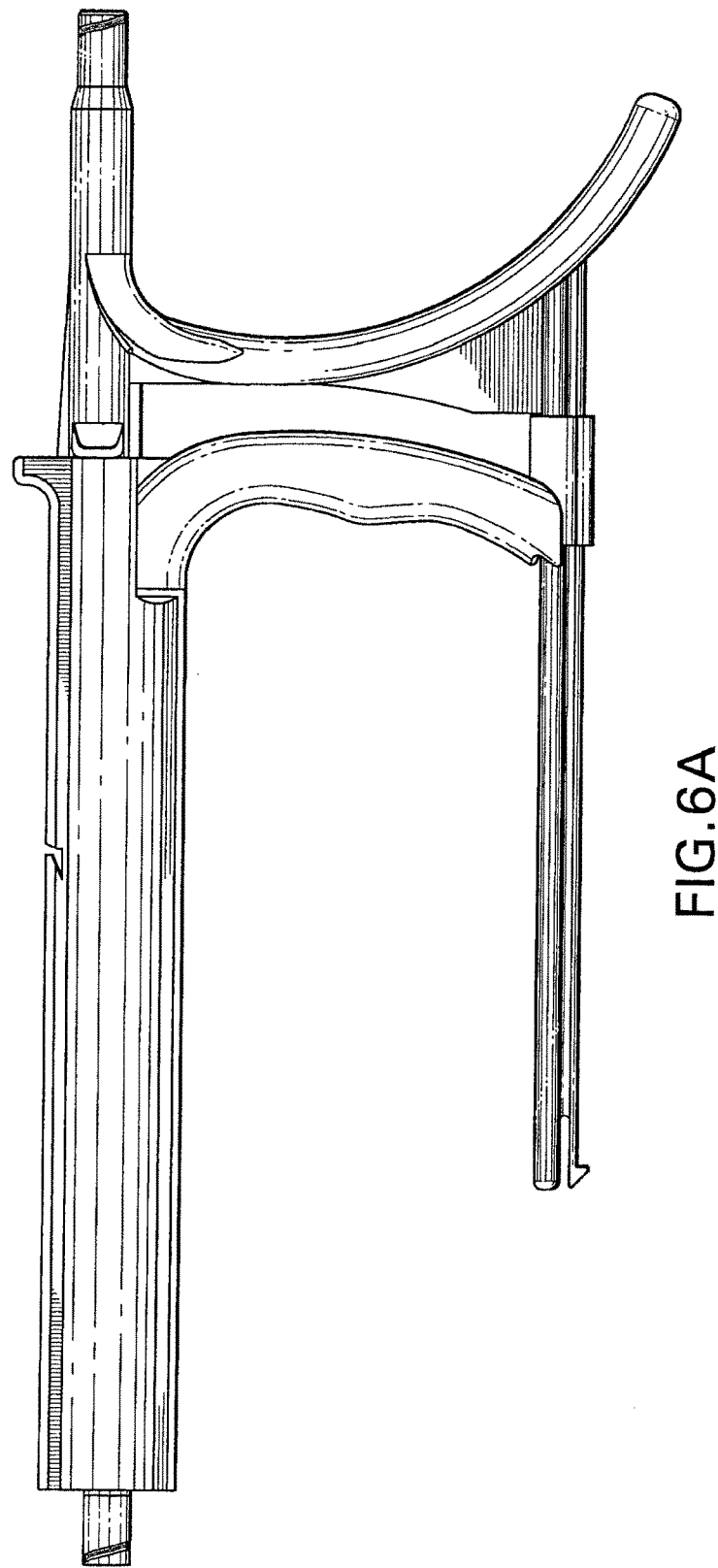
FIGS. 6A, 6B and 6C are perspective views of the exemplary deliver system 100 in a deployment configuration.
Figure 6B:
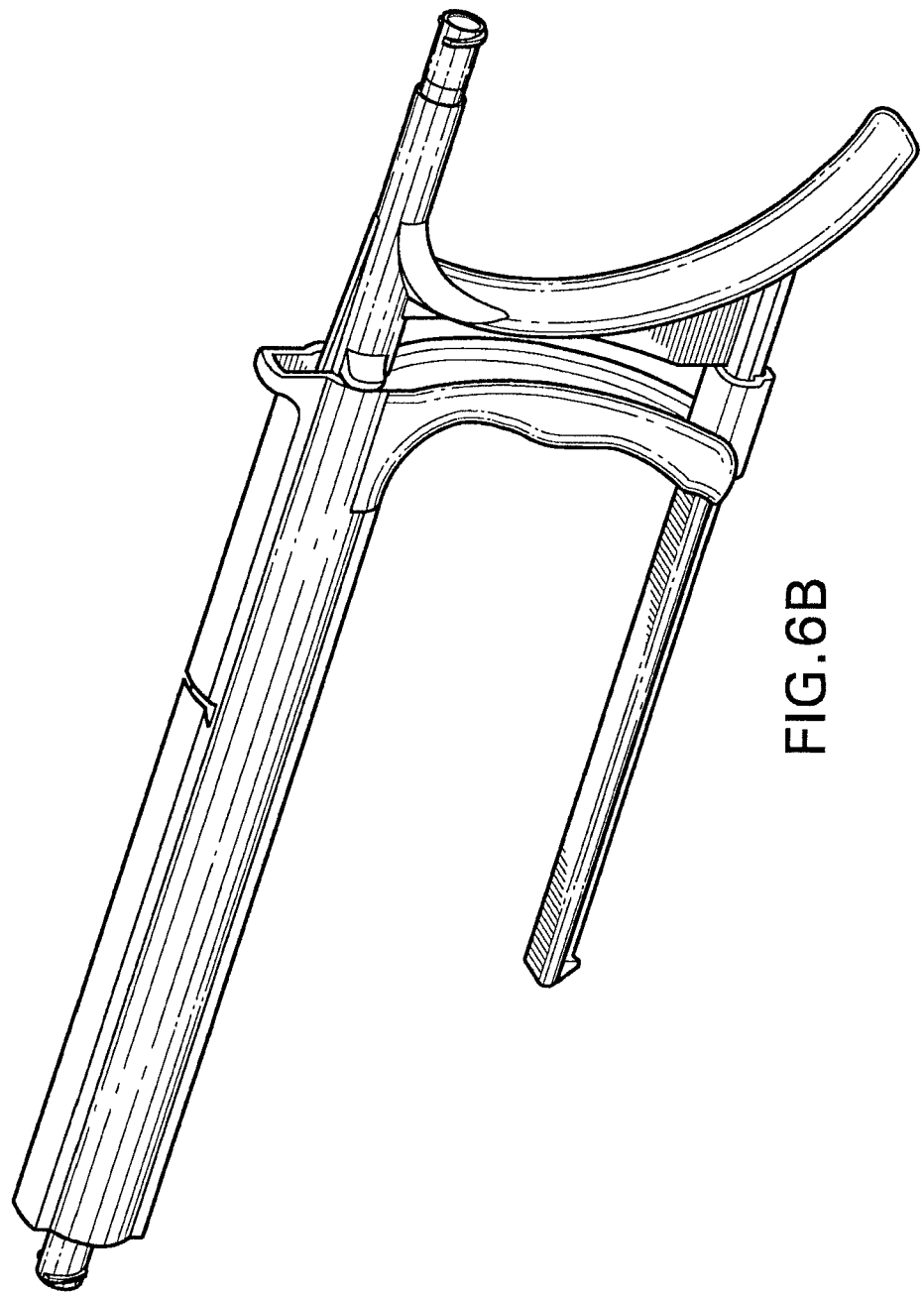
Figure 6C:
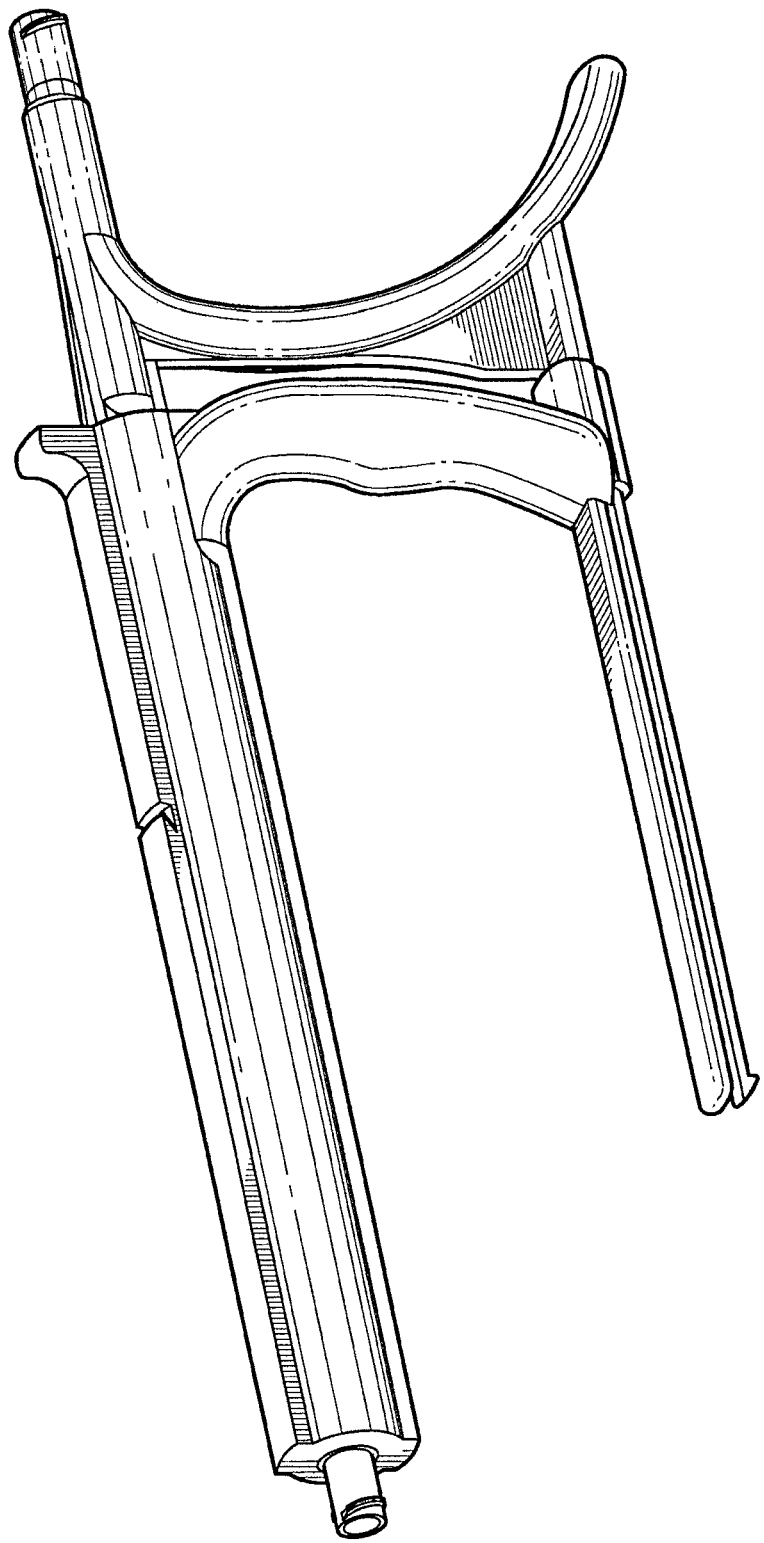

As shown in FIGS. 5A-5C, the second tubular member 30 contains a second tubular body 31 having a distal end 32 and a proximal end 33, and a second handle 34 for controlling movement of the second tubular member 30. The second tubular body 31 has a center lumen with a cross-sectional shape adopted to fit the outside contour of the first tubular body 21 and to slide longitudinally along the first tubular body 21. The second tubular member 30 is dissociable from the first tubular member 20.

As shown in FIGS. 1 and 4A-4C, the first tubular member 20 is connected to the base member 10 through an under-to-over connection. In other words, the first tubular member 20 is connected to the base member 10 by sliding the first tubular body 21 over the deployment extension 12 and the stabilizing ring 25 over the guiding extension 15. Similarly, the second tubular member 30 is also connected to the first tubular member 20 through an under-to-over connection, i.e., by sliding the second tubular body 31 over the first tubular body 21. A person of ordinary skill in the art would understand that the connection can be done in a number of sequences depending on the length of the implantable medical device to be delivered.

In one embodiment, the device 100 also includes an interlocking feature that allows the first tubular member 20 to be locked relative to the second tubular member 30. In one embodiment, the interlocking feature includes a locking tab 26 on the first tubular member 20 and a matching locking hole 33 on the second tubular member 30. As shown in FIG. 1, the locking tab 26 engages with the locking hole 36 to prevent the second tubular member 30 from falling off from the distal end of the first tubular member 20. The tab 26, however, has a beveled front side that allows the second tubular member 30 to slide over the locking tab 26 towards the proximate end 23 of the first tubular body. In another embodiment, the first tubular member 20 further contains a locking guide 27. In other embodiments, the device 100 further includes a second interlocking feature that allow the first tubular member 20 to be locked relative to the base member 10.

The distal ends of the deployment extension 12, the first tubular body 21 and the second tubular body 31 are configured to hold, contain or attach to an implantable device As used herein, the term "implantable device" is broadly interpreted to include stents and other medical devices that can be placed into a body lumen or body cavity. The implantable devices include implantable devices of the Stent Technology System (STS) family developed by Alveolus®, as well as implantable devices developed in accordance with U.S. patent application Ser. Nos. 10/190,770, 10/288,615, and 60/493,402 and international patent application Ser. No. PCT/DE02/01244, which are incorporated in their entirety by this reference.

The distal portion of the device can be configured to accommodate variable shafts to allow for ease of manufacturing and interchangeability of varying catheter diameters. In one embodiment, the distal end 14 of the deployment extension 12, the distal end 22 of the first tubular body 21, or the distal end 32 of the second tubular body 31 is configured such that a catheter may be removably attached to the distal end 14, 22 or 32. For example, the catheter may be screwed onto the distal end 14, 22 or 32, or coupled to the device by other conventional means such as a luer, hub, or other standard attachment mechanism.

As would be understand by one skilled in the art, the device 100 is a proportional release system. In certain embodiment, only the base member 10 and the first tubular member 20 are assembled together for deployment of implantable medical devices within a certain length range (e.g., less than about 50 mm). In other embodiment, the base member 10, the first tubular member 20, and the second tubular member 30 are assembled together for deployment of implantable medical devices having a greater length (e.g., about 50 mm to 100 mm). The multi-handle design allows for single-handed placement of the device 100. The parallel guide sheath offered by the deployment extension 12 and the guiding extension 15 provides stability and eliminates rotation of the first tubular member relative to the base member 10. The unique guide sheath also allows index finger rest during deployment. Finger guide for index finger rest for ease of stability and precision placement. In one embodiment, the first tubular member 20 and/or the second tubular member 30 are contoured on one side or on both sides for easy handling with the index finger.

The handles 11, 24 and 34 can be pulled together with a single hand. In one embodiment, the handles can be interlocked into each other in a male-and female connection. For example, the second handle 34 may have a hollow interior to accommodate the first handle 24. Similarly, the first handle 24 may have a hollow interior to accommodate the base handle 11. In one embodiment, both the second handle 34 and the first handle 24 may wrap around base handle 11 when fully compressed. In another embodiment, the second handle 34 is spaced at specific distances from the first handle 24 and the base handle 11 to optimize the closer comfort for the device and improve placement accuracy. The handles may have a beveled or rounded shape to improve ergonomics.

The device 100 may be made of any biocompatible material with suitable hardness and rigidity for the delivery of the implantable medical device. The device should have sufficient flexibility to adapt to anatomical curvatures without loss of ability to push or pull. In one embodiment, the device is made from a plastic material that can be molded to reduce production cost. In other embodiment, the individual parts of the device 100, such as the base member 10, the first tubular member 20 and the second tubular member 30 are interchangeable among different devices 100. The interchangeable parts allow the device 100 to be manufactured in different configurations, such as in a single handle (base member only), double handle (base member+first tubular member), triple handle (base member+first tubular member+second tubular member) or more complex configurations.

Figure 7:
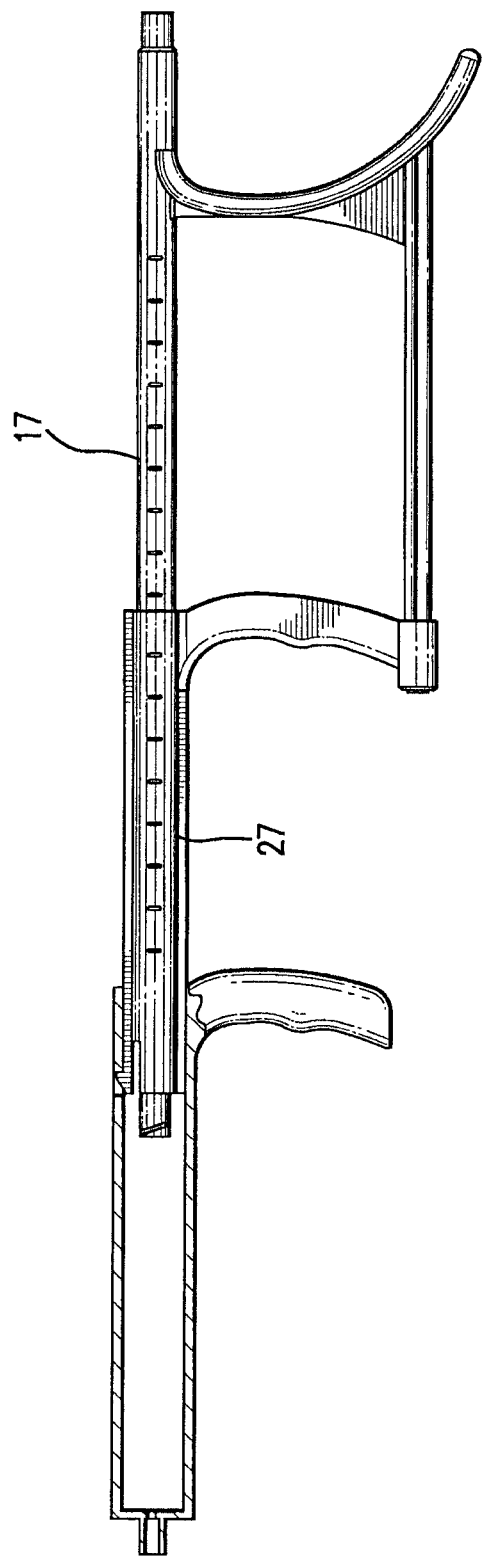
FIG. 7 shows a perspective view of another exemplary delivery system 100 in a pre-deployment configuration.

The diameter and the length of the deployment extension 12, the first tubular body 21 and/or the second tubular body 31, may be designed in compliant with the implantable devices to be delivered and the insertion procedure to be employed. The dimensions of the device must offer enough space for crimped implantable devices. Each individual part of the device should have smooth outer and inner surfaces to provide low friction between the moving parts. In certain embodiments, the deployment extension 12, as well as the first tubular body 21, has external measurement markers 17 and 27 for the determination of retraction distance (FIG. 7).

Also disclosed is a method for delivering an implantable medical device using the delivery device of the present invention. The method includes the steps of: attaching the first tubular member 20 to the base member 10 by sliding the first tubular body 21 over the implantable medical device and the deployment extension 12; attaching the second tubular member 30 to the base member 10 by sliding the second tubular body 31 over the first tubular body 21; attaching a proximate end of a catheter to the distal end 32 of the second tubular body 31, wherein an implantable medical device is attached to a distal end of the catheter; advancing the distal end of the catheter into a body lumen; retracting the first tubular member 20 and the second tubular member 30 towards the base member 10 to deploy the medical device. The order of retraction can vary. In one embodiment, the first tubular member 20 is retracted first, followed with the retraction of the second tubular member 30. In another embodiment, the second tubular member 30 is retraced first, followed with the retraction of the first tubular member 20.

The retraction of the first or second tubular member can be easily performed with a single hand using handles 24 or 34. In one embodiment, a user of the device 100 can hold the base handle 11, pull the first handle 24 towards the base handle 11 and hence retract the first tubular member 20. Alternatively, the user may first hold the first handle 24, pull the second handle 34 towards the first handle 24 and hence retract the second tubular member 30. As the second tubular body 31 is retracted over the first tubular body 21, the implantable device is exposed and deployed.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. An instrument for deploying an implantable medical device in a body lumen, the device comprising:
   a base member comprising a base handle;
   a deployment extension having a distal end and a proximate end, the proximate end is connected to the base handle;
   a first tubular member that fits over the deployment extension and is longitudinally slidable over the deployment extension, the first tubular member comprising: a first tubular body with a distal end and a proximate end, and a first handle for controlling movement of the first tubular member; and
   a second tubular member that fits over the first tubular member and is longitudinally slidable over the first tubular member, the second tubular member comprising: a second tubular body with a distal end and a proximate end, and a second handle for controlling movement of the second tubular member,
   wherein the first handle is located between the base handle and the second handle and wherein the distal ends of the deployment extension, the first tubular body, and the second tubular body are adapted to deploy an implantable medical device, and
   wherein the distal ends in each of the deployment extension, the first tubular body and the second tubular body comprises a screw, luer or hub that is configured to facilitate removable attachment of a catheter to the distal ends in each of the deployment extension, the first tubular body and the second tubular body.

2. The instrument of claim 1, wherein the base member further comprises a guiding extension, the guiding extension is connected to the base handle and extends in a direction parallel to the deployment extension.

3. The instrument of claim 1, wherein the base member further comprises a coupling device for a viewing device or a guide wire.

4. The instrument of claim 3, wherein the viewing device is an endoscope.

5. The instrument of claim 1, wherein the body lumen is a blood vessel.

6. The instrument of claim 1, wherein the body lumen is a bile duct.

7. The instrument of claim 1, wherein the first handle of the first tubular member comprises a stabilizing ring that fits over the guiding extension of the base member and is longitudinally slidable over the guiding extension.

8. The instrument of claim 1, wherein the first tubular member comprises interlocking means for attachment to the second tubular member.

9. The instrument of claim 8, wherein the interlocking means includes a locking tab on the first tubular body and a matching locking hole on the second tubular body.

10. The instrument of claim 1, wherein the base handle, the first handle and the second handle are beveled handles.

11. The instrument of claim 1, wherein the first tubular member has contoured sides to facilitate single-finger control of the first tubular member.

12. The instrument of claim 1, wherein the deployment extension of the base member further comprises a compression stopper to prevent the instrument from being over deployed.

13. The instrument of claim 1, wherein the implantable medical device is a stent.

14. A method for delivering an implantable medical device to a body lumen using the instrument of claim 1, comprising the steps of:
   attaching the first tubular member to the base member by sliding the first tubular body over the implantable medical device and the deployment extension;
   attaching the second tubular member to the base member by sliding the second tubular body over the first tubular body;
   attaching a proximate end of a catheter to the distal end of the second tubular body, wherein an implantable medical device is attached to a distal end of the catheter;
   advancing the distal end of the catheter into the body lumen; and
   retracting the first tubular member and the second tubular member towards the base member to deploy the implantable medical device in the body lumen.

15. The method of claim 14, wherein the retracting step includes:
   (1) retracting the second tubular member towards the proximate end of the first tubular member; and
   (2) retracting the first tubular member towards the proximate end of the base member.

16. The method of claim 14, wherein the retracting step includes:
   (1) retracting the first tubular member towards the proximate end of the base member, and
   (2) retracting the second tubular member towards the proximate end of the first tubular member.

17. The method of claim 14, further comprising attaching an endoscope to the base member.

18. The method of claim 14, wherein said implantable medical device is attached to a distal end of said catheter.

19. The method of claim 14, wherein the implantable medical device is a stent.

20. The method of claim 14, wherein the body lumen is a blood vessel or a bile duct.

\* \* \* \* \*